US008529771B2

(12) United States Patent
Fritz et al.

(10) Patent No.: US 8,529,771 B2
(45) Date of Patent: Sep. 10, 2013

(54) ACIDIC SLUDGE ADSORPTION OF DNT WASTEWATERS

(75) Inventors: Ruediger Fritz, Bernsdorf (DE); Renate Hempel, Ruhland (DE); Michael Zoellinger, Salach (DE); Anne-Kathrin Merten, Lauchhammer (DE); Doris Zschieschang, Guteborn (DE); Ina Homann, Senftenberg (DE); Annett Gersdorf, Hermsdorf (DE); Holger Allardt, Schwarzheide (DE); Reiner Reetz, Schwarzheide (DE); Elvira Flegel, Bernsdorf (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/514,648

(22) PCT Filed: Dec. 13, 2010

(86) PCT No.: PCT/EP2010/069519
§ 371 (c)(1),
(2), (4) Date: Jun. 8, 2012

(87) PCT Pub. No.: WO2011/082974
PCT Pub. Date: Jul. 14, 2011

(65) Prior Publication Data
US 2012/0234773 A1    Sep. 20, 2012

(30) Foreign Application Priority Data
Dec. 16, 2009  (EP) .................................... 09179505

(51) Int. Cl.
*C02F 1/20* (2006.01)
*C02F 3/00* (2006.01)
*C02F 9/00* (2006.01)
*C02F 1/68* (2006.01)

(52) U.S. Cl.
USPC ............ 210/750; 210/612; 210/631; 210/749

(58) Field of Classification Search
USPC .................................. 210/665, 612, 631, 749
See application file for complete search history.

(56) References Cited

U.S. PATENT DOCUMENTS

| 4,230,567 | A  |   | 10/1980 | Larbig |            |
|-----------|----|---|---------|--------|------------|
| 5,486,068 | A  | * | 1/1996  | Wilson | 405/129.25 |
| 5,762,802 | A  | * | 6/1998  | Carr et al. | 210/626 |
| 6,506,948 | B1 |   | 1/2003  | Sawicki |           |
| 7,470,826 | B2 | * | 12/2008 | Hermann et al. | 568/924 |
| 2004/0262238 | A1 | * | 12/2004 | Munnig et al. | 210/749 |
| 2004/0267062 | A1 |   | 12/2004 | Munnig et al. | |

FOREIGN PATENT DOCUMENTS

| DE | 1 221 994     | 7/1966  |
| DE | 101 43 800    | 8/2002  |
| EP | 0 005 203     | 11/1979 |
| EP | 0 953 546     | 11/1999 |
| EP | 1 493 730     | 1/2005  |
| EP | 1 496 043     | 1/2005  |
| WO | 2009 027416   | 3/2009  |
| WO | 2011 082977   | 7/2011  |
| WO | 2011 082978   | 7/2011  |

OTHER PUBLICATIONS

"Chemistry: The Molecular Science" Second Edition, Wm. C. Brown, 1997. p. 603.*
Wm. C. Brown "Chemistry: The Molecular Science," 1997, Second Edition, p. 603.*
U.S. Appl. No. 13/516,280, filed Jun. 15, 2012, Fritz, et al.
U.S. Appl. No. 13/511,256, filed May 22, 2012, Fritz, et al.
"Nitrobenzene and Nitrotoluenes," The Encyclopedia of Chemical Technology, Kirk-Othmer, Fourth Edition, vol. 17, pp. 133-152,(1996).
"Nitroverbindungen, aromatlsche," Ullmanns Encyklopaedie der technischen Chemie, Fourth Edition, vol. 17, pp. 386-387, (Aug. 30, 1979).
International Search Report Issued Mar. 28, 2011 in PCT/EP10/69519 Filed Dec. 13, 2010.

* cited by examiner

*Primary Examiner* — Nam Nguyen
*Assistant Examiner* — Claire Norris
(74) *Attorney, Agent, or Firm* — Oblon, Spivak, McClelland, Maier & Neustadt, L.L.P.

(57) ABSTRACT

A process for working up alkaline process wastewater from the nitration of aromatic compounds to mono-, di- and trinitroaromatics, said alkaline process wastewater having a pH of 7.5 to 13, comprising the steps of a) acidifying the alkaline process wastewater by adding concentrated sulfuric acid which originates from the workup of the aqueous, sulfuric acid-containing phase obtained in the nitration to a pH below 5, which forms a mixture A consisting of organic phase which separates out and acidic aqueous phase, b) contacting the mixture A with fresh sewage sludge, and c) removing the sewage sludge.

18 Claims, No Drawings

ACIDIC SLUDGE ADSORPTION OF DNT WASTEWATERS

This application is a National Stage of PCT/EP10/069519 filed Dec. 13, 2010 and claims the benefit of EP 09178505.4 filed Dec. 16, 2009.

The present invention relates to a process for working up alkaline process wastewater from the nitration of aromatic compounds, wherein the alkaline process wastewater is acidified by adding concentrated waste sulfuric acid which originates from the workup of the aqueous, sulfuric acid-containing phase obtained in the nitration, and the acidified process wastewater is contacted with fresh sewage sludge and the sewage sludge is then removed.

Aromatic nitro compounds such as mono- and dinitrotoluene are typically prepared by nitrating the corresponding aromatic compounds by means of a mixture of concentrated nitric acid and concentrated sulfuric acid, which is referred to as nitrating acid. This forms an organic phase which comprises the crude product of the nitration, and an aqueous phase which comprises essentially sulfuric acid, water of reaction and water introduced by the nitrating acid. The nitric acid is consumed almost completely in the nitration.

After separation of the two phases, the aqueous, sulfuric acid-containing phase, according to the technology of the nitrating process, is mixed again with fresh nitric acid, directly or after concentration, and used for nitration. However, at least some of the sulfuric acid must be discharged continuously or batchwise from the overall process in order to avoid concentration of impurities, especially of metallic salts (see also DE 10 143 800 C1). The impurities are, for example, impurities originally present in the nitric acid, and metal compounds which are leached out of the reactor and pipe materials under the highly corrosive conditions which exist in the course of reaction and workup of the aqueous phase.

In the concentration of the aqueous, sulfuric acid-containing phase obtained in the nitration, an aqueous distillate with low sulfuric acid content, referred to hereinafter as aqueous distillate of the sulfuric acid concentration, and a phase with a high sulfuric acid content, referred to hereinafter as concentrated sulfuric acid, are obtained. The portion of the concentrated sulfuric acid discharged from the nitrating process is also referred to hereinafter as waste sulfuric acid.

The crude product of the nitration of aromatic compounds, such as benzene, toluene, xylene, chlorobenzene, etc, to the corresponding nitroaromatics typically comprises, as well as the desired nitroaromatics such as nitrobenzene (NB) and dinitrobenzene (DNB), mono- and dinitrotoluene (MNT and DNT), nitrochlorobenzene (NCB) or nitroxylene, also small amounts of mono-, di- and trinitrophenols (referred to hereinafter as nitrophenols), mono-, di- and trinitrocresols (referred to hereinafter as nitrocresols) and mono-, di- and trinitroxylenols (referred to hereinafter as nitroxylenols) and other compounds comprising hydroxyl groups and nitro groups, and also mono- and dinitrobenzoic acids (referred to hereinafter as nitrobenzoic acids).

Aromatic nitro compounds which do not comprise a hydroxyl group or carboxyl group in the molecule are also referred to in the context of the invention as neutral nitroaromatics or neutral nitro species. Nitrophenols, nitrocresols, nitroxylenols and nitrobenzoic acids are also summarized hereinafter as hydroxynitroaromatics.

The crude product from the nitration has to be freed from the undesired by-products before further use. Typically, the by-products, after removal of the nitrating acid, are removed by multistage washing with acidic, alkaline and neutral washing liquid, generally in the sequence stated. The alkaline washing is typically performed with aqueous sodium hydroxide solution, an aqueous bicarbonate solution or an aqueous ammonia solution. The alkaline process wastewater which arises comprises nitrophenols, nitrocresols, nitroxylenols and nitrobenzoic acids, in the form of their water-soluble salts of the base used. They are typically present in a concentration of 0.2 to 2.5% by weight, based on the alkaline process wastewater. The alkaline process wastewater also comprises neutral nitro species formed in the nitration, especially reaction products. In addition, the alkaline wash also comprises a large proportion of the inorganic salts formed. The alkaline process wastewater therefore generally comprises 500 to 5000 ppm of nitrates, 500 to 5000 ppm of nitrite and a few hundred ppm of sulfate. Neutral nitro species are present in the alkaline process wastewater, typically in an amount of several 1000 s of ppm. The ingredients give rise to a chemical oxygen demand of 1000 to 20 000 mg/l.

The nitrophenols, nitrocresols, nitroxylenols, nitrobenzoic acids and in particular the salts thereof are intensely colored and highly toxic to the environment. Moreover, the nitrophenols and especially their salts, in relatively high concentrations or in substance, are explosives and have to be removed from the wastewater before the release thereof and disposed of in such a way that no risk to the environment from them. Since the aromatic nitro compounds have bactericidal properties overall and hence make biological purification of the wastewater impossible, purification or workup of the wastewater comprising aromatic nitro compounds is necessary.

Numerous processes for removal of the nitrophenols, nitrocresols, nitroxylenols, nitrobenzoic acids and the neutral nitroaromatics from the process wastewaters are described in the literature, for example extraction, adsorption, oxidation or thermolysis.

The Encyclopedia of Chemical Technology, Kirk-Othmer, Fourth Edition 1996, Vol. 17, p. 138 discloses an extraction process for removing nitrobenzene, in which the nitrobenzene dissolved in the wastewater at the appropriate temperature is removed by extraction with benzene. Benzene which has dissolved in the water is removed by stripping before the final treatment of the wastewater.

According to U.S. Pat. No. 6,506,948, the aqueous wash phases obtained in the nitration of benzene are extracted directly with toluene, each of the wastewater streams which arise being extracted separately. The toluene stream is subsequently conducted into the nitration process and converted. This leaves nitrocresols and nitrobenzoic acids dissolved in the alkaline wastewater stream, which subsequently have to be removed separately.

The dissolved nitroaromatics and hydroxynitroaromatics can additionally be removed in an acidic medium by extraction with an organic solvent (Ullmanns Enzyklopädie der technischen Chemie, $4^{th}$ edition, Volume 17, page 386).

The hydroxynitroaromatics present in the alkaline process wastewater can also be transferred by acidification to an organic phase which separates out and is subsequently removed. Such a process is described in EP 1 493 730 A1. In this process, the wastewater streams of the neutral and alkaline DNT washes and from the sulfuric acid concentration are mixed, such that a pH below 5 is established. The wastewater from the sulfuric acid concentration is the distillate of the sulfuric acid concentration with a sulfuric acid concentration of 0.2 to 1% by weight. In the course of acidification, an organic phase separates out, which is removed. The aqueous phase is supplied separately to a further wastewater treatment. In order to prevent the crystallization of the hydroxynitroaromatics, the apparatus used for the separation and removal has to be heated.

EP 0 005 203 describes a thermal process for working up wastewaters comprising hydroxynitroaromatics. In this process, the wastewaters, which comprise the hydroxynitroaromatics in the form of the water-soluble salts thereof, are heated with exclusion of air and oxygen under pressure to temperatures in the range of 150 to 500° C.

EP 0 953 546 discloses a thermal process for working up wastewater streams from nitrating plants, in which hydroxynitroaromatics and neutral nitroaromatics can be degraded simultaneously.

According to WO 2009/027416 A1, before the thermolytic treatment of the alkaline wastewaters from the nitration, the aromatic nitro compounds which do not comprise any hydroxyl groups and are present therein are removed by extraction.

A disadvantage of the processes described above is the often relatively high energy intensity of a thermolysis or of a steam stripping. When the alkaline process wastewater is adjusted to acidic pH and the organic phase which separates out, which comprises hydroxynitroaromatics and nitrobenzoic acids, is removed only by means of phase separation, the problem of "fouling" occurs. This means that the pumps and pipe systems used to remove the organic phase which separates out very rapidly become blocked by precipitating and crystallizing impurities, and there is therefore a high cleaning requirement.

In addition, it is known that, in the dinitrotoluene preparation, the dinitrotoluene-containing alkaline wastewater can be freed from the major portion of the 2,4- and 2,6-dinitrotoluene dissolved at 70° C. by an absorption on sewage sludge, before the hydroxynitroaromatics are digested by means of ozonization. The problem occurs here that the nitrocresols cannot be converted by the ozonization. In addition, the alkaline wastewater still comprises nitrate, which is only oxidized by ozone to nitrate and thus leads to an increased ozone demand. For instance, at a concentration of 3000 mg/l of nitrate in the alkaline process wastewater, about 25 to 40% of the ozone is consumed for the nitrite oxidation.

It is therefore an object of the present invention to provide a process which also enables the removal of the nitrocresols from the alkaline process wastewaters of the nitration of aromatic compounds, and reduces the energy expenditure and costs in the further treatment of the wastewater with conventional treatment methods.

This object is achieved by the following process for working up alkaline process wastewater from the nitration of aromatic compounds to mono-, di- and trinitroaromatics, said alkaline process wastewater having a pH of 7.5 to 13, comprising the steps of a) acidifying the alkaline process wastewater by adding concentrated sulfuric acid which originates from the workup of the aqueous, sulfuric acid-containing phase obtained in the nitration to a pH below 5, which forms a mixture A consisting of organic phase which separates out and acidic aqueous phase, b) contacting the mixture A with fresh sewage sludge, and c) removing the sewage sludge.

The alkaline process wastewater treated by the process according to the invention is highly depleted of neutral nitro species, nitrocresols and nitrobenzoic acids, which are difficult to degrade, and also of nitrite. The percentage lowering in the content of these compounds in an alkaline process wastewater treated in accordance with the invention from a plant for preparing dinitrotoluene, taking account of the dilution by the sewage sludge, is typically:

2,4-DNT: 50-57%,
2,6-DNT: 50-80%,
Sum (nitrocresols and nitrobenzoic acid): 70-90%,
Sum (nitrite): 85-95%.

A further advantage of the process according to the invention is that the entire amount of the waste sulfuric acid obtained in the acid concentration from the preparation process for the nitroaromatics can be used for the acidification of the alkaline process wastewater. The concentrated sulfuric acid comprises the salts obtained as a result of corrosion (pipelines) in the course of nitration, comprising Fe, Cr, Ni, Ta and traces of further heavy metals in the form of their sulfates. Typically, in the case of a rise in the salt concentration above 300 ppm, some of the acid has to be discharged from the process as so-called waste sulfuric acid and has to be disposed of or purified by other processes. The use of this waste sulfuric acid is therefore particularly advantageous, since the disposal or workup costs can be saved. The use of the concentrated waste sulfuric acid additionally leads to the effect that, when the alkaline process wastewater is acidified, a large portion of the nitrite dissolved in the alkaline process wastewater is protonated to nitrous acid, which then into nitric acid and nitrogen oxides. The nitrogen oxides can be removed and utilized, for example, in nitric acid preparation. In a preferred embodiment of the invention, the nitrogen oxides which separate out in the course of acidification are fed into the nitric acid recovery of the nitration plant and are therefore not lost to the process. The chemical oxygen demand of the wastewater stream treated by the process according to the invention is reduced significantly. The use of the concentrated waste sulfuric acid does not unnecessarily increase the amount of process wastewater to be cleaned, as is the case when dilute acid is used.

The process according to the invention is used for workup of alkaline process wastewater from the nitration of aromatic compounds. The aromatic compounds are preferably benzene, toluene, xylene, chlorobenzene and/or dichlorobenzene.

The alkaline process wastewater obtained from the one-stage or multistage washing of the crude product from the nitration with aqueous sodium hydroxide solution, aqueous carbonate or hydrogencarbonate solution or aqueous ammonia solution has, depending on the base used, a pH of 7.5 to 13, preferably 8 to 10 (measured at 60° C.).

According to the invention, the alkaline process wastewater is adjusted to a pH below 5, preferably of 0.5 to 3, by adding concentrated sulfuric acid which originates from the workup of the aqueous, sulfuric acid-containing phase obtained in the nitration. The pH figures are each based on measurement at 60° C. In the acidification of the alkaline process wastewater, an organic phase which comprises hydroxynitroaromatics, nitrobenzoic acids and neutral nitro species separates out. The acidified, originally alkaline process wastewater is referred to, together with the organic phase which separates out, as mixture A in the context of the invention.

The waste sulfuric acid used for acidification has a concentration of 85 to 95% by weight, preferably of 90 to 93% by weight. In a preferred embodiment, only waste sulfuric acid obtained in the nitration is added to the acidification in step a), particular preference being given to adding all of the waste sulfuric acid obtained in the nitration in step a). The addition of the concentrated sulfuric acid is advantageously controlled via online pH measurement.

The alkaline process wastewater is typically obtained at a temperature of 55 to 80° C. According to the invention, the alkaline process wastewater is also acidified at this temperature by adding the concentrated sulfuric acid. The mixing of the concentrated sulfuric acid with the alkaline process wastewater leads to significant evolution of gas. The gas mixture which separates out comprises $NO_x$, especially nitrogen monoxide, nitrogen dioxide and dinitrogen monoxide. If the alkaline wash water used was carbonate and/or hydrogencarbonate solution, the gas which separates out comprises typically 70 to 98.9% by volume of carbon dioxide and 1.1 to 30% by volume of nitrous gases (NOR). The gas mixture which separates out preferably comprises 80 to 98% by volume of carbon dioxide and 2 to 20% by volume of nitrous gases. When the process wastewater comprises, instead of alkali metal carbonate and/or alkali metal hydrogencarbonate, another base which does not form a gaseous component after acidification, the offgas consists exclusively of $NO_x$, typically 47 to 98% nitrogen monoxide, 1 to 47% nitrogen dioxide and 1 to 6% dinitrogen monoxide. The $NO_x$-containing offgases which separate out in the course of acidification are preferably removed and utilized in the nitric acid preparation. Particular preference is given to recycling the nitrogen oxides removed into the nitric acid recovery of the nitration plant. The gas mixture is typically fed into the absorption columns of the nitrogen monoxide and nitrogen dioxide absorption of the nitric acid recovery of the nitration plants. It is particularly advantageous when the entire gas mixture is recycled directly and without preceding removal of $CO_2$ and purification.

The absorbent used in step b) of the process according to the invention is fresh sewage sludge. In this context, "fresh" means that the sewage sludge originates from a sewage treatment plant and is yet to be used for absorption in the process according to the invention or a similar process. Preference is given in accordance with the invention to using biologically active sewage sludge which is still active to such an extent that the remaining proportion of the nitrite dissolved in the water can be oxidized to nitrate. In this way, an additional positive effect can be achieved, since the nitrite can be troublesome in a subsequent further treatment when, for example, nitrite first has to be oxidized to nitrate in the ozone treatment, thus unnecessarily consuming ozone.

Typically, the sewage sludge used as an absorbent in accordance with the invention has a solids content of 10-25 g/l.

According to the invention, the sewage sludge and the mixture A are contacted with one another for one minute up to two days, preferably for 2 minutes to 1.5 days.

Preferably in accordance with the invention, the sewage sludge and the mixture A are contacted with one another by conducting them into a common vessel. Further preferably, the mixture A and the sewage sludge are contacted in step b) with the aid of active and/or passive mixing elements. Suitable active and passive mixing elements are known to those skilled in the art. Active mixing elements include, for example, stirrers, ultrasound, shakers. The static mixing elements used may, for example, be channels and internals.

The alkaline process wastewater is typically obtained at a temperature of 50 to 80° C. According to the invention, the alkaline process water is also acidified at this temperature by addition of the concentrated waste sulfuric acid (step a). At the start, the mixture A, in the course of contacting with the sewage sludge (step b), has a temperature of 50 to 80° C. Preferably in accordance with the invention, the temperature of the alkaline process wastewater in step a) and of the mixture A at the start of step b) is 60 to 75° C.

The sewage sludge has, at the start of step b), on contacting with the mixture A, a temperature of 5 to 25° C., preferably of 8 to 15° C. This has the advantage that, as a result of the cooling effect and the solids content in the sewage sludge, the organic phase which separates out on acidification of the alkaline process wastewater precipitates out and is absorbed on the sewage sludge. In a preferred embodiment of the invention, the volume ratio of sewage sludge to the mixture A is selected such that a temperature of 30° C. or less is established. As a result of the significant cooling, the organic compounds which have a melting point above 30° C. precipitate out and separate out on the solids constituents of the sewage sludge.

The volume ratio of sewage sludge to the mixture A is typically 5:1 to 1:2, preferably 3:1 to 1:1.

After contacting the sewage sludge with the mixture A in step b), the sewage sludge is removed in step c). This is performed with the aid of customary apparatus known to those skilled in the art, for example with the aid of decanters or centrifuges; the sewage sludge is preferably removed with the aid of static separators.

The process according to the invention can be performed batchwise or continuously. Preferably in accordance with the invention, the process is performed continuously.

The process according to the invention is explained in detail hereinafter with reference to examples:

EXAMPLE 1

A 1000 mL stirred vessel with gas outlet and internal thermometer is initially charged with 400 mL of alkaline process wastewater from the production of dinitrotoluene at 60° C. The concentrations of DNT, nitrocresols and nitrobenzoic acids are listed in table 1. Subsequently, the process wastewater is admixed with 93% concentrated waste sulfuric acid until a pH of 2.5 is attained. The gas mixture which forms is passed through the gas outlet into an adjacent absorber cascade filled with 25% KOH. Once the gas formation has ended, 400 mL of fresh sewage sludge at 15° C. from Biology I of the sewage treatment plant of BASF Schwarzheide GmbH are added. The sewage sludge has a dry substance content of 20 g/L. A mixing temperature of 37° C. is established. Subsequently, the mixture is stirred for 30 minutes and transferred to a reservoir vessel. After centrifuging, the supernatant is analyzed. The results are likewise shown in table 1.

TABLE 1

| Component | Concentration before treatment [mg/l] | Concentration after treatment (inventive) [mg/l] | Reduction in amount [%] |
|---|---|---|---|
| 2,4-DNT | 556 | 214 | 62 |
| 2,6-DNT | 132 | 42.0 | 68 |
| Nitrocresols, Nitrobenzoic acid | 541 | 77.6 | 86 |

EXAMPLE 2

A 500 mL stirred vessel (B1) with gas outlet to an absorber (A1) and internal thermometer are continuously supplied with 1000 mL/h of alkaline process wastewater from the production of dinitrotoluene at 60° C., and continuously with 93% concentrated waste sulfuric acid from the acid concentration, controlled by means of an inline pH meter. The pH is adjusted to a value of 0.5. The gas mixture which forms is conducted via a gas outlet to an absorption column (A1) and thus withdrawn from the process. From the stirred vessel (B1), 525 mL of the acidified wastewater at 65° C. are conveyed continuously into the vessel (B2). 525 mL/h of the sewage sludge from Biology I of the sewage treatment plant of BASF Schwarzheide GmbH at 10° C. are introduced continuously into the stirred vessel B2. The sewage sludge has a dry substance content of 20 g/L. From the 5000 mL stirred vessel B2, which is 70% full, a volume flow of 1025 mL/h is conveyed continuously at 25° C. into a decanter (D) which, after the sewage sludge and the adsorbed organic components have settled out, affords a pretreated wastewater stream at 21° C. The vessel B2 is connected to the adsorption column (A1) via an offgas line. The wastewater stream from the decanter (D) is analyzed. The concentrations of DNT, nitrocresols and nitrobenzoic acids in the treated and untreated wastewaters are compared in table 2.

TABLE 2

| Component | Concentration before treatment [mg/l] | Concentration after treatment (inventive) [mg/l] | Reduction in amount [%] |
| --- | --- | --- | --- |
| 2,4-DNT | 556 | 186 | 67 |
| 2,6-DNT | 132 | 38.6 | 71 |
| Nitrocresols, Nitrobenzoic acid | 541 | 50.8 | 91 |

EXAMPLE 3

Example 3 is performed like example 2, with the difference that the pH, which is controlled by the metered addition of waste sulfuric acid from the acid concentration via an inline meter, is adjusted to 2.5. The concentrations of DNT, nitrocresols and nitrobenzoic acids before and after the inventive treatment are compared in table 3.

TABLE 3

| Component | Concentration before treatment [mg/l] | Concentration after treatment (inventive) [mg/l] | Reduction in amount [%] |
| --- | --- | --- | --- |
| 2,4-DNT | 556 | 264 | 53 |
| 2,6-DNT | 132 | 59.4 | 55 |
| Nitrocresols, Nitrobenzoic acid | 541 | 155 | 71 |

The invention claimed is:

1. A process for treating alkaline process wastewater from a nitration, comprising:
   a) adding, to the wastewater, concentrated sulfuric acid from an aqueous sulfuric acid containing phase of the nitration, thereby acidifying the wastewater to a pH below 5, and thereby obtaining a mixture consisting of organic phase, which separates out, and acidic aqueous phase,
   b) contacting the mixture with sewage sludge, and
   c) removing the sewage sludge,
   wherein the nitration is of an aromatic compound to a mono-, di-, or trinitroaromatic, or combination thereof, and
   an initial pH of the wastewater is from 7.5 to 13,
   wherein a temperature of the sewage sludge when first contacting the mixture is from 5 to 25° C.

2. The process of claim 1, wherein the concentrated sulfuric acid has a concentration of from 85 to 95% by weight.

3. The process of claim 1, wherein adding the concentrated sulfuric acid comprises adding all waste sulfuric acid of the nitration.

4. The process of claim 1, wherein adding the concentrated sulfuric acid adjusts the pH to from 0.5 to 3.

5. The process of claim 1, wherein contacting the mixture with the sewage sludge comprises contacting the mixture and the sewage sludge for from 1 minute to 2 days.

6. The process of claim 1, wherein the aromatic compound is benzene, toluene, xylenol, chlorobenzene, dichlorobenzene, or a mixture thereof.

7. The process of claim 1, wherein a temperature of the alkaline process wastewater when adding concentrated sulfuric acid and a temperature of the mixture when first contacting the fresh sewage sludge are each from 50 to 80° C.

8. The process of claim 1, wherein contacting the mixture with sewage sludge comprises contacting a volume ratio of sewage sludge to the mixture, thereby producing a second mixture with a temperature of 30° C. or less.

9. The process of claim 1, wherein contacting the mixture with sewage sludge comprises contacting a volume ratio of sewage sludge to the mixture of from 5:1 to 1:2.

10. The process of claim 1, wherein contacting the mixture with fresh sewage sludge comprises contacting with an active mixing element, a passive mixing element, or both.

11. The process of claim 1, further comprising:
   removing a nitrogen oxide that separated out during adding concentrated sulfuric acid, and
   employing the nitrogen oxide in nitric acid preparation.

12. The process of claim 1, further comprising:
   removing a nitrogen oxide that separated out after adding concentrated sulfuric acid, and
   recycling the nitrogen oxide into a nitric acid recovery in a nitrating plant.

13. The process of claim 1, wherein removing the sewage sludge comprises removing with a static separator.

14. The process of claim 1, wherein the process is in continuous mode.

15. The process of claim 2, wherein the concentrated sulfuric acid has a concentration of from 90 to 93% by weight.

16. The process of claim 7, wherein the temperature of the alkaline process wastewater when adding concentrated sulfuric acid and the temperature of the mixture at when first contacting the fresh sewage sludge are each from 60 to 75° C.

17. The process of claim 1, wherein the temperature of the sewage sludge when first contacting the mixture is from 8 to 15° C.

18. The process of claim 9, wherein contacting the mixture with sewage sludge comprises contacting a volume ratio of sewage sludge to the mixture of from 3:1 to 1:1.

* * * * *